United States Patent [19]
Schoenberg et al.

[11] Patent Number: 5,965,594
[45] Date of Patent: Oct. 12, 1999

[54] ANTIMICROBIAL LIQUID PRESERVATIVE SOLUTIONS AND PROCESS FOR PREPARATION

[75] Inventors: Thomas G. Schoenberg, Lemont; Richard J. Otterson, Olympia Fields; Dennis Abbeduto, Chicago Heights, all of Ill.

[73] Assignee: McIntyre Group, Ltd.

[21] Appl. No.: 09/050,787

[22] Filed: Mar. 30, 1998

[51] Int. Cl.$^6$ .......................... A01N 43/50; A01N 47/10
[52] U.S. Cl. .................. 514/389; 514/390; 514/478; 514/479
[58] Field of Search .................. 514/389, 390, 514/478, 479

[56] References Cited

U.S. PATENT DOCUMENTS

| | | | |
|---|---|---|---|
| 4,844,891 | 7/1989 | Rosen et al. | 424/76.4 |
| 5,037,843 | 8/1991 | Schoenberg | 514/389 |
| 5,428,050 | 6/1995 | Merianos | 514/390 |
| 5,496,842 | 3/1996 | Merianos | 514/389 |
| 5,552,425 | 9/1996 | Merianos | 514/390 |
| 5,616,722 | 4/1997 | Schoenberg et al. | 548/319.1 |
| 5,631,273 | 5/1997 | Merianos | 514/389 |
| 5,693,849 | 12/1997 | Nowak | 560/167 |

OTHER PUBLICATIONS

"Cosmetic Preservatives", excerpt from *A Complete Guide To The McIntyre Group Product Line*, 18, McIntyre Group, Ltd. (1996).

Mulberry, G.K., et al., "Rapid Screening Methods for Preservative Efficacy Evaluations", *Cosmetics & Toiletries*, 102, 47–50, 52–54 (1987).

Muscatiello, M.J., "CTFA's Preservation Guidelines", *Cosmetics & Toiletries*, 108, 53, 56–59 (1993).

Parsons, T., "A Microbiology Primer for the Microbiology Manager", *Cosmetics & Toiletries*, 105, 73–77 (1990).

"Preservation Mixture Encyclopedia Update", *Cosmetics & Toiletries*, 108, 89–91 (1993).

Parker, M. S., "Preservatives in Combination", *Soap, Perf., Cosmet.*, 223–224 (Apr. 1973).

Gruening, R., "IPBC Preservative Combination Systems for Material Protection", *Cosmetics & Toiletries®*, 112, 59–60, 63–65 (1977).

"BIOCARB® C 450 Preservative for Cosmetics", Product Bulletin, G+G International, Inc. (undated).

"PHENAGON™ PDI", Product Bulletin (Nov. 1997) and Material Safety Data Sheet (Jan. 5, 1998), McIntyre Group, Ltd.

Godfrey, D., "In search of Parabens", reproduced from SPC magazine available in "Cosmetic Science and Technology On–line," Apr. 17, 1997, http://www.cotpubco.demon-.co.uk/nipab.html.

Steinberg, D.C., Excerpts from *Preservatives for Cosmetics*, C&T Ingredient Resource Series, 2, 10–11, 13–17, 30–31, published by Cosmetics & Toiletries® Magazine (1996).

"Liquid Germall® Plus", Product Bulletin, ISP Sutton Laboratories (undated).

*Primary Examiner*—Jose' G. Dees
*Assistant Examiner*—Sabiha N. Qazi
*Attorney, Agent, or Firm*—Olson & Hierl, Ltd.

[57] ABSTRACT

Improved liquid antimicrobial solutions useful as preservative additives to personal care preparations, particularly cosmetic formulations and the like, are provided which comprise 1,3-dimethylol-5,5-disubstituted hydantoin, liquid aromatic alcohol, and iodoalkynyl alkyl carbamate. A preferred antimicrobial solution can be prepared by producing the 1,3,dimethylol-5,5-disubstituted hydantoin in situ in the selected liquid aromatic alcohol and then adding to the resulting solution the previously prepared iodoalkynyl alkyl carbamate. The solutions are surprisingly water dispersible and display broad spectrum antimicrobial effectiveness, particularly antifungal effectiveness, at a relatively low usage concentration in a cosmetic medium.

26 Claims, No Drawings

ANTIMICROBIAL LIQUID PRESERVATIVE SOLUTIONS AND PROCESS FOR PREPARATION

FIELD OF THE INVENTION

This invention lies in the field of antimicrobial solutions of formaldehyde substituted hydantoin and iodoalkynyl alkyl carbamate and of methods for the preparation thereof.

BACKGROUND OF THE INVENTION

Antimicrobial combinations of formaldehyde substituted hydantoin, particularly 1,3-dimethylol-5,5-dimethyl hydantoin (abbreviated for convenience as DMDMH), with various selected other antimicrobial agents are desirable additives for use in a variety of personal care preparations, particularly cosmetics. Multiple usage personal care preparations, such as shampoos, skin lotions and the like, are especially prone to exposure to bacterial contamination during repeated opening of the container for product usage.

Although DMDMH is a broad spectrum antimicrobial, it is primarily active against bacteria and less active against fungi. Thus, to fully achieve broad spectrum antimicrobial activity, DMDMH is frequently combined with a second component that is particularly active against fungi. Also, the two components in combination should preferably be water soluble and achieve a greater antimicrobial effectiveness than either component used separately at equivalent concentrations.

Conventionally, the second, anti-fungal component employed is a paraben (or paraben mixture). The parabens are esters of parahydroxy benzoic acid (para acid). The parabens can only function in the water phase of a product but are not readily water soluble. Moreover, the parabens can be partially or fully inactivated by hydrogen bonders, such as highly ethoxylated compounds, e.g., polysorbates, by cellulose derivatives, proteins and the like which are frequent ingredients in personal care preparations. There is an ongoing need, therefore, for alternative antifungal components for use in combination with DMDMH.

Recent favorable experience and manufacturer response by the personal care industry has been achieved with the use of 3-iodo-2-propynyl butyl carbamate (abbreviated for convenience as IPBC), a potent fungicide but weak biocide. Consequently, a demand for combinations of DMDMH and IPBC has arisen.

Some dry powder blends of DMDMH and IPBC are disclosed by Merianos in U.S. Pat. No. 5,428,050 and No. 5,496,842 and by Rosen et al., in U.S. Pat. No. 4,844,891. However, for additive use in personal care preparations, such dry blends either must be first dissolved, usually in water before being admixed with such a preparation, or must be carefully directly added to a preparation and dissolved therein. Not only is either of such addition sequence time-consuming, but also each sequence is unpredictable and unreliable as to whether or not homogeneous dissolution and distribution will be achieved. Further, such dry blends present handling problems, such as dusting, spillage and the like.

Moreover, IPBC has a limited solubility in water of reportedly about 160–200 parts per million (0.016–0.02%). Thus, as the amount of IPBC increases in dry blends of DMDMH and IPBC, the water solubility of the blend decreases. Merianos, in U.S. Pat. No. 5,428;050 and No. 5,496,842, teaches, for example, that a high weight ratio of DMDMH to IPBC of upwards of 100:1 to 2000:1 in a DMDMH:IPBC powder blend is needed for water solubility and that at DMDMH:IPBC weight ratios below 100:1, it is difficult to uniformly distribute the iodopropynyl compound in aqueous use compositions.

A liquid composition containing predispersed DMDMH and IPBC, therefore, appears to offer the advantages of being readily admixable with aqueous or nonaqueous preparations and of achieving homogeneous distribution in the resulting finished system.

Some liquid compositions of DMDMH and IPBC are described by Merianos in U.S. Pat. No. 5,496,842,. No. 5,552,425 and No. 5,631,273 which are prepared by using the foregoing water soluble, dry blend of DMDMH and IPBC predispersed in propylene glycol or 1,3-butylene glycol. The two foregoing alkylene glycols taught by Merianos are readily water soluble aliphatic diols but have little or no recognized antimicrobial activity, themselves, at use concentrations below about 10 weight percent in the finished preparation. Moreover, the Merianos liquid compositions require that the water soluble, dry blend of DMDMH and IPBC have a high weight ratio of DMDMH to IPBC ranging upwards from 100:1 to 2000:1.

Unfortunately, as the weight of DMDMH in the dry blend increases and the weight of the IPBC decreases, antifungal effectiveness decreases, as shown by tests and evaluations of the antifungal effectiveness of these dry blends reported by Merianos in Tables 21 and 22 of U.S. Pat. No. 5,428,050 and U.S. Pat. No. 5,496,842. Consequently, high levels of broad spectrum antimicrobial activity, especially against the yeast, *Candida albicans* (Ca), was not achieved by using such dry blends at the low usage concentrations that are desired for acceptable commercial practicality in personal care preparations. This presents a problem because the maximum amount of DMDMH containing antimicrobial compositions used in personal care preparations is limited in many countries by regulation.

Thus, the art needs a new and improved liquid composition for DMDMH and IPBC which, when admixed with an aqueous medium at a usage concentration preferably of no more than about one weight percent produces broad spectrum antimicrobial activity, and especially antifungal activity.

The present invention provides such a new and improved liquid composition.

SUMMARY OF THE INVENTION

The present invention relates to new and improved liquid antimicrobial solutions useful as preservative additives to personal care preparations, particularly cosmetic formulations and the like. The antimicrobial solutions of this invention display broad spectrum antimicrobial effectiveness, and especially antifungal effectiveness, at a relatively low usage concentration in an aqueous cosmetic medium.

The antimicrobial solutions are made by combining components comprising a 5,5-disubstituted hydantoin which has in at least one, preferably both, of the 1 and 3 positions a methylol substituent and the 5,5 substituents are selected from phenyl or lower alkyl groups; a liquid aromatic alcohol having the formula:

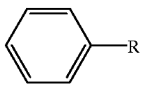

where R is selected from the group consisting of:

—CH₂OH, —OCH₂OH, —OCH₂CH₂OH,

—CH₂CH₂OH, —OC₃H₆OH, and —C₃H₆OH;

an iodoalkynyl alkyl carbamate having the formula:

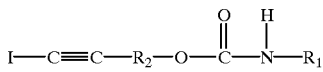

where $R_1$ is an alkyl group containing no more than about 20 carbon atoms, and $R_2$ is an alkylene group containing from 1 through 4 carbon atoms; and less than about 15 weight percent water on a total solution weight basis.

The methylol substituted 5,5-disubstituted hydantoin preferably is prepared in situ in a liquid medium containing the aromatic alcohol by first thermally reacting dissolved formaldehyde with dissolved 5,5-disubstituted hydantoin, and then, iodoalkynyl alkyl carbamate, having been separately prepared, can be dissolved in the reaction medium. Preferably, the weight ratio of the methylol substituted 5,5-disubstituted hydantoin to the carbamate is in the range of from about 60:1 to about 80:1.

In particular, the present invention relates to new and improved liquid antimicrobial solutions of in situ prepared 1,3,dimethylol-5,5-disubstituted hydantoin (DMDMH) in an antimicrobial liquid phenylic or benzylic alcohol which here also acts as a solvent for 3-iodo-2-propynyl butyl carbamate (IPBC). The concentration of DMDMH in such liquid aromatic alcohol preferably is in the range of about 25 to about 75 weight percent (on a total liquid solution basis), more preferably at least about 30 weight percent. The aromatic alcohol preferably is phenoxyethanol and the concentration of the DMDMH to IPBC is preferably in the range of about 65:1 to about 78:1.

In an alternative method embodiment, an antimicrobial solution of this invention can be prepared by direct dissolution of separately prepared DMDMH and IPBC in a liquid medium comprising the aromatic alcohol, heating as needed to achieve a homogenous solution. Such a direct dissolution procedure, however, is less commercially practical for the present inventive compositions. For one thing, the preliminary preparation of DMDMH as a dry powder requires a plurality of manufacturing steps which substantially add to production costs. For another thing, handling dry powders presents dusting problems at the time dissolution thereof is attempted.

Although Merianos in U.S. Pat. No. 5,496,842, No. 5,552,425 and No. 5,631,273 teaches a direct dissolution procedure of dry blends of DMDMH and IPBC in propylene glycol or 1,3-butylene glycol for making liquid compositions, the limited water solubility characteristics of the aromatic alcohols present different dispersibility, stability and liquidity problems than those of such water soluble alkylene glycols.

Although the technology of Schoenberg et al., U.S. Pat. No. 5,616,722 is useful for making relatively concentrated solutions of DMDMH in phenylic or benzylic alcohol, the thermal conditions therein taught for dissolving parabens in such a solution are generally not optimal for dissolving IPBC.

The present invention, therefore, beneficially provides an optimized process for dissolving IPBC in a solution of in situ prepared DMDMH in liquid aromatic alcohol so that commercial production of the inventive compositions is directly achieved in a minimum of steps. Further, the present invention achieves liquid antimicrobial solutions that are readily water dispersible without having to preliminarily prepare dry powder blends of DMDMH and IPBC employing high weight ratios of DMDMH to IPBC of 100:1 to 2000:1 as taught by Merianos, U.S. Pat. No. 5,496,842.

Surprisingly, a liquid antimicrobial solution of this invention can be admixed with an aqueous medium, to achieve, at a relatively low dilution concentration in such a medium, a high level of broad spectrum antimicrobial activity, and antifungal activity, in particular. Further surprising, such solutions are substantially water dispersible and homogeneous distribution is characteristically observed.

Beneficially, the antimicrobial solutions of this invention offer an optimized solution of DMDMH and IPBC that can be homogeneously dispersed in an aqueous medium containing known paraben inactivating ingredients for achieving broad spectrum antimicrobial activity, and antifungal activity, in particular, even at low dispersed concentration,. The antimicrobial solutions of this invention thus offer an alternative to paraben containing liquid antimicrobial solutions for use in formulations that contain paraben inactivating ingredients. Additionally beneficial, each component of the present inventive antimicrobial solution is microbiologically active and can be dispersed in both aqueous and nonaqueous media.

Other features, advantages and the like will be apparent to those skilled in the art from the present specification and the appended claims.

DETAILED DESCRIPTION

The term "antimicrobial solution" as used herein refers to a composition that can kill, prevent, inhibit or retard the growth and reproduction of microorganisms when it is included in a product medium at a concentration sufficient to prevent spoilage or prevent the growth of an inadvertently added microorganism (that is, an antimicrobially effective amount). Such an antimicrobial solution generally extends the useful life of a product without contributing otherwise to the claimed efficacy of the product and is useful as a preservative composition for personal care preparations.

The term "personal care preparations" includes cosmetics, toiletries, skin and hair cleansers, cosmeceuticals, over-the-counter pharmaceutical products, and the like intended for topical use for beautifying or grooming skin and hair.

The term "water dispersible" as used herein in connection with the antimicrobial solution means that when the composition is admixed with water at a relatively low concentration of no more than about 1 weight percent, a substantially clear solution produced within one minute.

Preferred antimicrobial solution embodiments of this invention are prepared by producing methylolated 5,5-disubstituted hydantoin in situ by thermally reacting dissolved formaldehyde with dissolved 5,5-disubstituted hydantoin in the selected aromatic alcohol and then adding to the resulting solution the previously prepared iodoalkynyl alkyl carbamate. The reaction with formaldehyde introduces methylol groups bound to the nitrogen atom at each of the 1 and/or 3 positions of the hydantoin ring and 5,5-disubstituted hydantoin which can be so methylolated can have substituents selected from phenyl and lower alkyl groups. The term "lower alkyl" means that the alkyl group contains no more than about 7 carbon atoms.

Exemplary 5,5-disubstituted hydantoin include 5,5-dimethyl hydantoin (DMH), 5-methyl-5-ethylhydantoin, 5,5-diethylhydantoin, 5,5-diphenylhydantoin, 5-methyl-5-phenylhydantoin, 5,5-pentamethylenehydantoin and the like known in the art as possessing broad spectrum bactericidal activity. DMH is particularly preferred for preparing 1,3-dimethylol-5,5-dimethyl hydantoin (DMDMH).

The liquid aromatic alcohols usable in the practice of the present invention are characterized by the formula:

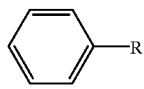

(1)

wherein R is selected from the group consisting of —CH$_2$OH, —OCH$_2$OH, —OCH$_2$CH$_2$OH, —CH$_2$CH$_2$OH, —OC$_3$H$_6$OH, and —C$_3$H$_6$OH.

Preferred formula (1) compounds are phenoxyethanol (presently most preferred), benzyl alcohol, phenethyl alcohol, phenoxyisopropyl alcohol and mixtures thereof, all of which are known to have antimicrobial activity.

In one preferred method of this invention, one initially dissolves formaldehyde, added as substantially anhydrous paraformaldehyde, in at least one aromatic alcohol of formula (1). With respect to paraformaldehyde, the term "substantially anhydrous" denotes paraformaldehyde which is at an active concentration of above about 90 weight percent, preferably at about 95 weight percent or more based on total starting paraformaldehyde composition. Alternatively, the formaldehyde can be added as formalin, preferably methanol free and at a concentration of at least about 30 weight percent formaldehyde. Paraformaldehyde is preferred.

If it is desirable to intentionally include water, beyond that formed as a product of reaction, a portion of the total desired water content can be included in the liquid medium.

The resulting liquid medium preferably contains an amount of at least about 2 weight percent, and, more preferably in the range of from about 10 to about 25 weight percent of total calculated formaldehyde on a 100 weight percent total liquid medium basis.

This resulting liquid medium is then heated to a temperature of no more than about 50° C., preferably to a temperature of no more than about 45° C. Thereafter a 5,5-disubstituted hydantoin (such as above characterized) is admixed into (and dissolved in) the so-heated liquid medium to produce a reaction mixture. In this reaction mixture, the amount of the 5,5-disubstituted hydantoin present is at least sufficient to produce in the reaction mixture an initial calculated mole ratio of formaldehyde to the substituted hydantoin of about 1:1 to about 3:1 and, more preferably, in the range of about 1.5:1 to about 2.1:1.

Next, the resulting reaction mixture is heated under autogenous pressure conditions (in a sealed reactor to avoid loss of volatile components) to a temperature of no more than about 110° C. for a period sufficient for a liquid phase condensation reaction to ensue between the paraformaldehyde and the 5,5-disubstituted hydantoin. Characteristically, the condensation product contains a mixture of methylol substituted 5,5-disubstituted hydantoin with the methylol substituents being in the 1 and/or 3 positions. However, the reaction conditions influence the condensation product produced so that very high yields of 1,3-dimethylol substituted 5,5-disubstituted hydantoin (DMDMH) can be produced, as preferred.

The temperature of the resulting reaction mixture is maintained until the condensation reaction is substantially complete as determined by the point where the amount of free formaldehyde present in the reaction mixture is no more than about 2.5 weight percent, preferably no more than about 1 weight percent, based on total reaction mixture weight. To reach such a free formaldehyde content, it may be desirable to add additional 5,5-disubstituted hydantoin as needed to the reaction mixture.

Thereafter, the resulting reaction mixture can be cooled to a temperature below about 40° C., preferably to a temperature in the range of about 25° C. to about 35° C., and then dissolved therein is an iodoalkynyl alkyl carbamate characterized by the formula:

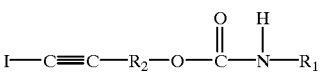

(2)

where R$_1$ is an alkyl group containing no more than about 20 carbon atoms, and R$_2$ is an alkylene group containing from 1 through 4 carbon atoms.

A description of a method of manufacturing such iodoalkynyl carbamates of high purity, for example, can be found in Nowak, U.S. Pat. No. 5,693,849, the relevant disclosures of which are incorporated herein by reference. A presently preferred iodoalkynyl alkyl carbamate, without being limited thereto, is 3-iodo-2-propynyl butyl carbamate (IPBC). IPBC is commercially available as a 97–99% powder under the trademark BIODOCARB C450 from G+G International, Inc. (Basking Ridge, N.J.), and under the trademark OMACIDE IPBC-100 from Olin Corporation (Stamford, Conn.).

When the resulting antimicrobial solution is substantially homogeneous and visually clear, it can be further cooled to about ambient room temperature, if necessary. Optionally, this solution can be filtered to remove any particulates and to further clarify the solution.

Preferably, in such a product antimicrobial solution, the total amount of methylol substituted 5,5-disubstituted hydantoin ranges from about 25 to about 75 weight percent while the amount of formula (1) aromatic alcohol preferably ranges from about 20 to about 70. Preferably the weight ratio of methylol substituted 5,5-disubstituted hydantoin to iodoalkynyl alkyl carbamate is in the range of from about 60:1 to about 80:1. The balance of up to 100 weight percent of the solution can comprise unreacted components (formaldehyde and 5,5-disubstituted hydantoin) and no more than about 15 weight percent total water (either intentionally added or as water of reaction). If desired, as those skilled in the art will appreciate, the water of reaction can be removed by stripping or the like, to produce a substantially anhydrous product solution, preferably before the dissolution therein of the iodoalkynyl alkyl carbamate. Alternatively, the total water content of the product antimicrobial solution can be adjusted after dissolution of the iodoalkynyl alkyl carbamate In general, antimicrobial solution products of this invention are physically clear and remain so on storage. The inventive solutions also demonstrate useful broad spectrum antimicrobial activity, especially antifungal activity, even at usage concentrations of no more than about one weight percent, preferably no more than about 0.8 weight percent, in an aqueous medium capable of supporting microbial growth and containing paraben inactivating ingredients.

Known paraben inactivating ingredients include, without limitation, highly ethoxylated compounds such as polysorbates, and surfactants, proteins and derivatives thereof, cellulose derivative, lecithin and the like.

Presently preferred product antimicrobial solutions of this invention are characterized by having the following compositional ranges of components as shown in Table I below:

TABLE I

SOLUTION COMPOSITIONS

| Component | Weight Percent | | |
| --- | --- | --- | --- |
| | Broad Range | Preferred Range | Most Preferred Range |
| (a) Methylol substituted 5,5-disubstituted hydantoin | 20–75[1] | 25–60 | 30–40[2] |
| (b) Aromatic alcohol of formula (1) | 20–70 | 35–65 | 50–60[3] |
| Weight ratio of (a) to Carbamate of formula (2) | 60:1–80:1 | 65:1–78:1 | 70:1–75:1 |
| Water | 0–15 | 2–12 | 6–10 |

Table I Footnotes
[1]The starting 5,5-disubstituted hydantoin is 5,5-dimethyl hydantoin and the formaldehyde condensate therewith contains a mole ratio of formaldehyde to 5,5-dimethyl hydantoin in the range of about 1:1 to about 3:1 and a content of 1,3-dimethylol-5,5-dimethyl hydantoin of at least about 10 weight percent on a total substituted hydantoin weight basis.
[2]The starting 5,5-disubstituted hydantoin is 5,5-dimethyl hydantoin and the formaldehyde condensate therewith contains a mole ratio of formaldehyde to 5,5-dimethyl hydantoin in the range of about 1.5:1 to about 2.1:1 and a content of 1,3-dimethylol-5,5-dimethyl hydantoin of at least about 25 weight percent on a total substituted hydantoin weight basis.
[3]The starting aromatic alcohol comprises phenoxyethanol.

Those skilled in the art appreciate that greater or smaller amounts of individual components can be used without departing from the spirit and scope of the present invention.

A presently most preferred practice for the present inventive process is to produce a product antimicrobial solution in which the antimicrobial liquid aromatic alcohol comprises phenoxyethanol and the 5,5-disubstituted hydantoin comprises 5,5-dimethyl hydantoin. Also, in such a product antimicrobial solution, the mole ratio between the formaldehyde and the substituted hydantoin is preferably such that the condensation product comprises on a 100 weight percent total condensation product basis at least about 10 weight percent 1,3-dimethylol-5,5-dimethyl hydantoin (DMDMH), and more preferably about 25 weight percent on a total condensate hydantoin weight basis.

The amount of IPBC can be in the range of about 0.25 to about 1.25 weight percent, preferably in the range of about 0.3 to about 1 weight percent, most preferably in the range of about 0.4 to about 0.6 weight percent, of the total solution. Preferably, the weight ratio of DMDMH to IPBC is in the range of from about 60:1 to about 80:1.

A particularly preferred product solution contains at least about 30 weight percent DMDMH, at least about 50 weight percent phenoxyethanol and IPBC at a weight ratio of DMDMH to IPBC in the range of about 65:1 to about 78:1, most preferably in the range of about 70:1 to about 75:1.

In a preferred solution embodiment IPBC is readily dispersed and dissolved in phenoxyethanol containing in situ prepared DMDMH. In an alternative preferred embodiment, separately prepared DMDMH powder and IPBC each can be directly dissolved in phenoxyethanol, warming if necessary, to fully dissolve the IPBC and form a substantially clear, homogenous solution.

Antimicrobial solution products of this invention are substantially water dispersible. Surprisingly at a concentration of no more than about one weight percent in water at ambient room temperature, an antimicrobial solution containing a weight ratio of DMDMH to IPBC of about 70:1 formed which was initially hazy but within less than about one minute formed a substantially clear solution.

An antimicrobial solution of the present invention preferably has a pH in the range of about 5 to about 7, more preferably in the range of about 5.5 and about 6.5. If it is desirable to adjust the pH of a product antimicrobial solution, the adjustment can be accomplished by addition to the solution of an aqueous acidifying agent or alkalizing agent, as the case may be.

The terms "alkalizing agent" and "acidifying agent" each respectively refer to any commercially practical alkaline base or acid that does not interfere with the preparation of the antimicrobially active preservative solution and which, if present in an amount in excess of that needed for pH adjustment, is preferably soluble in the solvent medium and is substantially nontoxic to humans. Without being limited thereto, a preferred alkalizing agent is sodium hydroxide and a preferred acidifying agent is citric acid, both of which are commonly used in the personal care arts.

In the personal care arts, the microorganisms of greatest concern include, but are not limited to, molds, such as *Aspergillus niger* (An); yeasts, such as *Candida albicans* (Ca); gram-positive microorganisms, such as *Staphylococcus aureus* (Sa); nonfermentative gram-negative rod microorganisms, such as *Pseudomonas aeruginosa* (Pa) and fermentative gram-negative rod microorganisms, *Escherichia coli* (Ec).

A discussion of the various microorganisms and why they are of particular concern in personal care products generally can be found in the literature. See, for example, Muscatiello M. J., "CTFA's Preservation Guidelines," *Cosmetics & Toiletries*, 108, 53, 56–59 (1993), the relevant portions of which are incorporated herein by reference. Likewise, those skilled in the art are familiar with the various challenge tests employed for determining antimicrobial activity and minimum effective levels. See, for example, the discussions of various testing by Mulberry G. K. et al. in "Rapid Screening Methods for Preservative Efficacy Evaluations," *Cosmetics & Toiletries*, 102, 47–50, 51–54 (1987) and by Parsons, T, in "A Microbiology Primer for the Microbiology Manager," *Cosmetics & Toiletries*, 105, 73–77 (1990), the relevant portions of each being incorporated herein by reference.

It is known that monomethylol and dimethylol condensation products of 5,5-dimethyl hydantoin have broad spectrum antibacterial activity at usage concentrations of about 0.01 to about 1 weight percent but are less effective against fungi. Phenoxyethanol, per se is a weak biocide, but is reportedly most effective against gram-negative bacteria at usage concentrations of about 0.5 to about 2 weight percent. IPBC is a strong fungicide but is a weak bactericide, especially against *Pseudomonas aeruginosa* (Psa).

A discussion of the antimicrobial efficacy of the foregoing as cosmetic preservatives can be found in the literature. See, for example, Steinberg, D. C., *Preservatives for Cosmetics*, (C&T Ingredient Resource Series), Allured Publishing Corp., (Carol Stream, Ill.), the relevant portions of which are incorporated herein by reference.

It has been surprisingly found that addition and dissolution of IPBC improves the product solution antimicrobial activity still further to enhance the product solution bacteriostatic activity at low usage concentration against fungi, particularly the yeast, *Candida albicans* (Ca). Further, the inventive antimicrobial solutions were useful as preservative compositions in aqueous mediums containing known paraben inactivating ingredients, such as, for example, shampoos containing protein derivatives, polysorbates and the like.

The preservation efficacy of the inventive antimicrobial solution was determined by in vitro modified microbial challenge testing when it was employed in an aqueous product formulation known to support microbial growth. A modified microbial challenge test protocol for rapidly screening the microbial efficacy in an aqueous medium was adapted from the standard method of the United States Pharmacopeia (USP) and the method of the Cosmetic, Toiletry and Fragrance Association (CTFA). The foregoing modified method allowed for a shortened challenge test period of multiple use cosmetic products, such as shampoos, and consisted of inoculating the product formulation with different types of microorganisms which are representative of the most frequently encountered contaminants in cosmetic and personal care formulations.

Briefly described, an aqueous formulation capable of microbial growth was separately inoculated with a mixed bacterial culture of Pa, Sa and Ec, and individually with the fungi, Ca and An. Microbial growth then was periodically determined over an incubation period of at least 7 to 14 days. For an antimicrobial solution to pass the modified microbial challenge test, i.e., demonstrate antimicrobial effectiveness, viable bacteria concentration had to be reduced to about 0.1 weight percent of the original total bacterial count (i.e., average count of microbial colony forming units (cfu) per milliliter (ml) of test product) within 7 days and remain at or below that level throughout the total 14 day test period. To pass the modified microbial challenge test for fungi (yeast and mold), the average fungal growth count had to remain at (static) or below the inoculation level by 7 days and not exceed that level for the remainder of the test.

For product preservation, an average mixed bacterial count of less than 10 cfu/ml was generally considered to be adequate. The effective amount of antimicrobial preservative solution for adequately preserving the test product by the 7 to 14 day time period was deemed to be the minimum effective level (MEL). It is recognized in the trade that a formulation can be unnecessarily over preserved when the amount of preservative employed exceeds the amount required for adequate preservation.

As indicated above, and as demonstrated and illustrated by the following examples, the preferred solution compositions of Table I are characterized by broad spectrum microbial efficacy, and by being particularly effective against the yeast, Ca. As illustrated in the examples below, it was surprisingly found that, in an aqueous shampoo product model containing known paraben inactivating ingredients and generally prone to microbial growth, an antimicrobial solution of this invention achieved adequate preservation at an MEL of no more than about 0.8 weight percent of the total shampoo composition. Further surprising was that adequate preservation and antifungal effectiveness was achieved in such a cosmetic medium at low usage levels of no more than about 0.005% IPBC.

The following Examples illustrate methods and liquid antimicrobial solutions of this invention with generally preferred ingredients and procedural steps, but are not intended to limit the invention.

EXAMPLE 1

This example illustrates a method embodiment for preparing a liquid antimicrobial solution containing IPBC dissolved in phenoxyethanol containing about 35 weight percent in situ prepared DMDMH from the following component mixture:

| Component | Weight Percent |
| --- | --- |
| 1. Phenoxyethanol | 56.8 |
| 2. Paraformaldehyde Prills (95%) | 11.5 |
| 3. 5,5-dimethyl hydantoin (96%) | 25.2 |
| 4. IPBC (97–99%) | 0.5 |
| 5. Water    q.s. to | 100 |

Component no. 1 and about 60% of the total amount of component no. 5 desired in the solution were charged into a sealable reaction vessel outfitted with a jacket for heating or cooling and a sampling port and were admixed with stirring to form a liquid mixture. Component no. 2 was then dissolved with stirring in the liquid mixture and the resulting liquid medium was then heated to about 40° C. Component no. 3 was then added slowly to the so-heated liquid medium to form a reaction mixture. The reactor was then sealed to prevent loss of volatile components, and formaldehyde in particular, from the reaction mixture during heating. The resulting reaction mixture was then heated to about 105° C. and maintained at that temperature, until, by periodic analysis, the desired amount of DMDMH was produced and the free formaldehyde concentration was no more than about 2.5 weight percent of the total weight of the reaction mixture.

The reaction mixture was then cooled to a temperature in the range of about 30° C. to about 35° C. Component no. 4 was then admixed into the so-cooled reaction mixture with stirring until the resulting reaction mixture was a homogeneous and substantially clear liquid composition. Thereafter, the liquid composition was further cooled to about 25° C., adjusted for pH and total water content by adding the remaining amount of component no. 5, as needed, and the resulting antimicrobial solution collected.

The product liquid antimicrobial solution had a pH in the range of about 5.5 and about 6.5. The assayed amount of free formaldehyde was in the range of about 1 to about 2.5 weight percent and the assayed amount of total water was between about 6 and about 10 weight percent on a total solution basis.

EXAMPLE 2

This example illustrates the preparation of one antimicrobial solution embodiment by direct dissolution method.

| Component | Weight Percent |
| --- | --- |
| 1. Phenoxyethanol | 56.5 |
| 2. DMDMH (100%) | 35 |
| 3. IPBC (97–99%) | 0.5 |
| 4. Water    q.s. to | 100 |

Component nos. 2 and 3 were admixed directly with component no.s 1 and 4 with stirring until a substantially clear, homogeneous solution was produced.

EXAMPLE 3

This example illustrates the antimicrobial efficacy of an inventive antimicrobial solution (3A) prepared generally by the direct dissolution method of Example 2 compared to two commercial paraben containing antimicrobial solutions and a commercial dry blend of DMDMH/IPBC employing a model shampoo formulation having the composition shown in the following Table 1.

TABLE 1

| Component | Weight Percent |
| --- | --- |
| Sodium laurylethersulfate (70%) (Note a) | 30 |
| Cocamide DEA (Note b) | 3 |
| Hydrolyzed collagen (Note c) | 1 |
| Water q.s. to | 100 |

Note a: MACKOL 70NS (2.2 moles Ethylene oxide), McIntyre Group, Ltd., University Park, IL
Note b: MACKAMIDE C, McIntyre Group, Ltd., University Park, IL
Note c: PEPTEIN 2000, anhydrous, Hormel Foods, Austin, MN As described below, each of the indicated weight percent (wt %) of antimicrobial solution additive was incorporated into the model shampoo with stirring. The microbial efficacy of the antimicrobial solution in the model shampoo was assessed against that of the model shampoo without antimicrobial additive (control) by carrying out the modified microbial challenge test previously described for the inhibition of the growth of *Aspergillus niger* (An) ATCC No. #16404; *Candida albicans* (Ca) ATCC No. #10231; and a mixed bacterial culture of *Staphylococcus aureus* (Sa) ATCC No. #6538, *Pseudomonas aeruginosa* (Pa) ATCC No. #9027 and *Escherichia coli* (Ec) ATCC No. #8739.

For microbial evaluation, a series of about 20 ml of model shampoo were each separately inoculated to contain about 105 to 106 cfu/ml of An, of Ca and of the mixed bacterial culture of Sa, Pa, Ec organisms. The inoculated model shampoo samples were individually plated out in tryptic soy agar medium with lecithin and Polysorbate 80 for assessing bacterial growth and in potato dextrose agar (acidified) for assessing fungi growth. Following platings at day 1 and day 7, and incubation, readings of the number of colony forming units per milliliter (cfu/ml) were made. After the day 7 plating, the model shampoo samples were reinoculated and plated at day 8 and day 14, incubated and readings taken again.

An antimicrobial solution was judged effective and the model shampoo product adequately preserved when the average concentrations of viable mixed bacteria were reduced to no more than 0.1% of the initial concentration (i.e., MEL point) and the average concentration of viable fungi (yeasts and molds) remained at or below the initial concentrations by the 7 to 14 day test period.

A series of model shampoos were separately prepared to contain on a total shampoo weight basis, 0% (unpreserved control), about 0.4 wt %, about 0.5 wt %, and about 0.6 wt % use concentration of inventive liquid antimicrobial solution (3A). The average antimicrobial efficacy data for the inventive antimicrobial solution (3A) over the 14 day total test period was as shown in Table 2.

TABLE 2

| Wt % Liq. (3A) in Model Shampoo | Org. | Colony Forming Units (cfu/ml) | | | |
| --- | --- | --- | --- | --- | --- |
| | | Day 1 | Day 7 | Day 8 | Day 14 |
| 0.4 | An | 4,700 | <100 | 24,000 | <100 |
| | Ca | <100 | <100 | <100 | <100 |
| | Sa,Pa,Ec | 230 | <10 | <10 | <10 |
| 0.5 | An | 1,500 | <100 | <100 | <100 |
| | Ca | <100 | <100 | <100 | <100 |
| | Sa,Pa,Ec | <10 | <10 | <10 | <10 |
| 0.6 | An | <100 | <100 | <100 | <100 |
| | Ca | <100 | <100 | <100 | <100 |
| | Sa,Pa,Ec | <10 | <10 | <10 | <10 |
| 0 (control) | An | 430,000 | 230,000 | 660,000 | 850,000 |
| | Ca | 1,100 | 3,100 | 18,000 | 3,100 |
| | Sa,Pa,Ec | 35,000 | >3 × 10$^6$ | >3 × 10$^6$ | >3 × 10$^6$ |

On a total shampoo basis, the three concentrations of inventive antimicrobial solution (3A) evaluated in the model shampoo respectively represented, on an active basis, a usage concentration of DMDMH in the range of about 0.14 to about 0.21 wt %, of phenoxyethanol in the range of about 0.22 to about 0.34 wt % and of IPBC in the range of about 0.002 to about 0.003 wt %. Adequate preservation and surprisingly high antifungal effectiveness, especially against Ca, was achieved at a usage concentration of 0.002 wt % IPBC.

Included for comparison, a second series of model shampoos were separately prepared employing a commercial liquid paraben containing preservative solution, (PARAGON® III, McIntyre Group, Ltd., University Park, Ill., prepared generally by the procedure taught in U.S. Pat. No. 5,616,722, containing about 30% DMDMH, about 48% phenoxyethanol, about 11% methylparaben, about 4% propylparaben and about 7% water. The model shampoos were separately prepared to contain, on a total shampoo weight basis, the commercial preservative solution at a use concentration of about 0.5 wt %, about 0.6 wt %, about 0.7 wt % and about 0.8 wt %. The average antimicrobial efficacy data, assessed during the same foregoing modified microbial challenge study, was as shown in Table 3.

TABLE 3

| Model Shampoo w/ Wt % PARAGON® III | Org. | Colony Forming Units (cfu/ml) | | | |
| --- | --- | --- | --- | --- | --- |
| | | Day 1 | Day 7 | Day 8 | Day 14 |
| 0.5 | An | 1,000 | <10 | 15,000 | <10 |
| | Ca | 15,000 | <100 | 4,000 | <100 |
| | Sa,Pa,Ec | 240 | <10 | <10 | <10 |
| 0.6 | An | 420 | <10 | 2,200 | <10 |
| | Ca | <100 | <100 | 1,000 | <100 |
| | Sa,Pa,Ec | <10 | <10 | <10 | <10 |
| 0.7 | An | <10 | <10 | 30 | <10 |
| | Ca | <100 | <100 | <100 | <100 |
| | Sa,Pa,Ec | <10 | <10 | <10 | <10 |
| 0.8 | An | <10 | <10 | <10 | <10 |
| | Ca | <1,000 | <1,000 | <1,000 | <1,000 |
| | Sa,Pa,Ec | <10 | <10 | <10 | <100 |
| 0 (control) | An | 430,000 | 230,000 | 660,000 | 850,000 |
| | Ca | 1,100 | 3,100 | 18,000 | 3,100 |
| | Sa,Pa,Ec | 35,000 | >3 × 10$^6$ | >3 × 10$^6$ | >3 × 10$^6$ |

On a total shampoo basis, the four concentrations of paraben containing antimicrobial solution in the model shampoos respectively represented, on an active basis, a usage concentration of DMDMH in the range of about 0.15 to about 0.24 wt %, of phenoxyethanol in the range of about 0.24 to about 0.38 wt %, and of a total paraben concentration in the range of about 0.075 to about 0.12 wt %.

Also included for comparison, a third series of model shampoos were prepared employing a commercial liquid paraben containing preservative solution, (PARAGON®, McIntyre Group, Ltd., prepared generally by the procedure taught in U.S. Pat. No. 5,037,843, containing about 35% DMDMH, about 50% propylene glycol and about 15% methylparaben). The model shampoos were prepared to separately contain, on a total shampoo basis, the commercial paraben containing preservative solution at a use concentration of about 0.5% and about 0.6 wt %. The average antimicrobial efficacy data, assessed during the same foregoing modified microbial challenge study, was as shown in Table 4.

TABLE 4

| Model Shampoo w/ Wt % PARAGON ® | Org. | Colony Forming Units (cfu/ml) | | | |
|---|---|---|---|---|---|
| | | Day 1 | Day 7 | Day 8 | Day 14 |
| 0.5 | An | 90 | <10 | <10 | <10 |
| | Ca | <100 | <100 | <100 | <100 |
| | Sa,Pa,Ec | 60 | <10 | <10 | <10 |
| 0.6 | An | <10 | <10 | <10 | <10 |
| | Ca | <100 | <100 | <100 | <100 |
| | Sa,Pa,Ec | <10 | <10 | <10 | <10 |
| 0 (control) | An | 430,000 | 230,000 | 660,000 | 850,000 |
| | Ca | 1,100 | 3,100 | 18,000 | 3,100 |
| | Sa,Pa,Ec | 35,000 | >3 × $10^6$ | >3 × $10^6$ | >3 × $10^6$ |

On a total shampoo basis, the two concentrations of paraben containing antimicrobial solution evaluated respectively represented, on an active basis, a usage concentration of DMDMH in the range of about 0.175 to about 0.21 wt %, of propylene glycol in the range of about 0.25 to about 0.3 wt %, and of paraben in the range of about 0.075 to about 0.09 wt %.

For additional comparison, a fourth series of model shampoos were prepared employing a commercial preservative dry powder blend, (GLYDANT PLUS®, Lonza, Inc., Fair Lawn, N.J., described generally in U.S. Pat. No. 4,844,891, reportedly containing 95% DMDMH and 5% IPBC). The model shampoos were prepared to separately contain the commercial dry powder blend at a use concentration of about 0.05 wt %, about 0.1 wt %, and about 0.15 wt %. The average antimicrobial efficacy data for the powder commercial blend, assessed during the same foregoing modified microbial challenge study, was as shown in Table 5.

TABLE 5

| Model Shampoo w/ wt % GLYDANT PLUS ® | Org. | Colony Forming Units (cfu/ml) | | | |
|---|---|---|---|---|---|
| | | Day 1 | Day 7 | Day 8 | Day 14 |
| 0.05 | An | 610,000 | 6,000 | 480,000 | 35,000 |
| | Ca | 9,300 | <100 | 3,900 | <100 |
| | Sa,Pa,Ec | 4,500 | <10 | 260 | <10 |
| 0.1 | An | 140,000 | <1,000 | 92,000 | <1,000 |
| | Ca | 2,300 | <1,000 | 3,000 | <10 |
| | Sa,Pa,Ec | 160 | <10 | 90 | <10 |
| 0.15 | An | 3,000 | <1,000 | 400,000 | 270,000 |
| | Ca | <100 | <100 | <100 | <100 |
| | Sa,Pa,Ec | <10 | <10 | 90 | <10 |
| 0 (control) | An | 430,000 | 230,000 | 660,000 | 850,000 |
| | Ca | 1,100 | 3,100 | 18,000 | 3,100 |
| | Sa,Pa,Ec | 35,000 | >3 × $10^6$ | >3 × $10^6$ | >3 × $10^6$ |

On a total shampoo basis, the three concentrations of powder blend in the model shampoos respectively represented, on an active basis, a usage concentration of DMDMH in the range of about 0.048 to about 0.142 wt %, and of IPBC in the range of about 0.0025 to about 0.0075 wt % in the shampoo product.

The results show that the inventive antimicrobial solution (4A) achieved adequate preservation of the model shampoo at a minimum effective level (MEL) of about 0.4 wt % use concentration, and that desirable antifungal effectiveness, especially against Ca was achieved at a usage concentration of about 0.002% IPBC. These results show that the inventive antimicrobial solution achieved good antifungal activity at a lower MEL than was required with the liquid paraben containing compositions. The data also show that greater and more consistently effective broad spectrum antimicrobial activity, especially against fungi, was achieved with the inventive antimicrobial solution (3A) than with the commercial powder blend of DMDMH and IPEC at equivalent DMDMH or equivalent IPBC usage concentrations.

EXAMPLE 4

This example illustrates the antimicrobial efficacy of a liquid antimicrobial solution (4A) of this invention prepared generally by the direct dissolution method of Example 2 compared to a commercial liquid paraben containing antimicrobial solution and a commercial aqueous DMDMH solution.

To demonstrate the antimicrobial effectiveness of the solution, a "mild" shampoo model having the composition shown in Table 6 was prepared.

TABLE 6

| Component | Weight Percent |
|---|---|
| Ammonium lauryl sulfate | 8 |
| Disodium oleamido MEA sulfosuccinate | 2 |
| Hydrolyzed collagen (Note c, Table 1) | 2.2 |
| Cocamide DEA (Note b, Table 1) | 1 |
| Polysorbate 80 | 2 |
| Water     q.s. to | 100 |

A series of model shampoos were prepared to separately contain, on a total shampoo weight basis, 0% (unpreserved control), about 0.2 wt %, about 0.4 wt %, and about 0.6 wt % use concentrations of the liquid antimicrobial solution (4A), dissolved in the shampoo with heating to form a substantially clear shampoo product. The microbial efficacy of antimicrobial solution (4A) was assessed by following the procedure of the modified challenge test described in Example 3. The average microbial efficacy data after the 14 day test was as shown in Table 7.

TABLE 7

| wt % Liq. (4A) in Model Shampoo | Org. | Colony Forming Units (cfu/ml) | | | |
|---|---|---|---|---|---|
| | | Day 1 | Day 7 | Day 8 | Day 14 |
| 0.2 | An | 200,000 | 300 | 260,000 | 450 |
| | Ca | 850 | <10 | 2,000 | <10 |
| | Sa,Pa,Ec | 2,800 | 170 | 4,200 | 160 |
| 0.4 | An | 400 | <10 | 900 | <100 |
| | Ca | 90 | <10 | 30 | <10 |
| | Sa,Pa,Ec | 690 | <10 | 110 | <10 |
| 0.6 | An | <100 | <100 | <100 | <100 |
| | Ca | <10 | <10 | <10 | <10 |
| | Sa,Pa,Ec | <10 | <10 | <10 | <10 |

TABLE 7-continued

| wt % Liq. (4A) in Model | | Colony Forming Units (cfu/ml) | | | |
|---|---|---|---|---|---|
| Shampoo | Org. | Day 1 | Day 7 | Day 8 | Day 14 |
| 0 (control) | An | 710,000 | 690,000 | >3 × $10^6$ | 1.3 × $10^6$ |
| | Ca | 60,000 | 98,000 | 1,300 | 57,000 |
| | Sa,Pa,Ec | 13,000 | >3 × $10^6$ | >3 × $10^6$ | >3 × $10^6$ |

On a total shampoo basis, the three concentrations of inventive antimicrobial solution (4A) evaluated respectively represented, on an active basis, a usage concentration of DMDMH in the range of about 0.07 to about 0.21 wt %, of phenoxyethanol in the range of from about 0.11 to about 0.34 wt %, and of IPBC in the range of from about 0.001 to about 0.002 wt %. The data show that the liquid antimicrobial solution (4A) achieved adequate preservation at a an MEL of about 0.2% and that a high level of antifungal effectiveness, especially against Ca, was noted even at a 0.001 wt % IPBC usage level.

Included for comparison, a second series of model mild shampoos were separately prepared employing a commercial liquid paraben containing preservative solution (PARAGON®, McIntyre Group, Ltd., University Park, Ill. containing about 35% DMDMH, about 50% propylene glycol and about 15 weight percent methyl paraben). These model shampoos were prepared to separately contain, on a total shampoo basis, about 0.2 wt %, about 0.4 wt %, and about 0.6 wt % of the commercial paraben containing antimicrobial solution. The microbial effectiveness of the model shampoo was assessed during the challenge test in the foregoing study and the average microbial efficacy data was as shown in Table 8.

TABLE 8

| Model Shampoo w/ wt % PARAGON® | Org. | Colony Forming Units (cfu/ml) | | | |
|---|---|---|---|---|---|
| | | Day 1 | Day 7 | Day 8 | Day 14 |
| 0.2 | An | 660,000 | 21,000 | 500,000 | 140,000 |
| | Ca | 63,000 | 13,000 | 210,000 | 33,000 |
| | Sa,Pa,Ec | 3,800 | 70 | 5,400 | 100 |
| 0.4 | An | 970 | 70 | 4,900 | 280 |
| | Ca | 3,500 | 360 | 5,600 | 1,000 |
| | Sa,Pa,Ec | 1,100 | 10 | 1,100 | <10 |
| 0.6 | An | 10 | <10 | 20 | <10 |
| | Ca | <10 | <10 | 60 | <10 |
| | Sa,Pa,Ec | 90 | <10 | 390 | <10 |
| 0 (control) | An | 710,000 | 690,000 | >3 × $10^6$ | 1.3 × $10^6$ |
| | Ca | 60,000 | 98,000 | 1,300 | 57,000 |
| | Sa,Pa,Ec | 13,000 | >3 × $10^6$ | >3 × $10^6$ | >3 × $10^6$ |

On a total shampoo basis, the three concentrations of paraben containing solution respectively represented, on an active basis, a usage concentration of DMDMH in the range of about 0.074 to about 0.22 wt % DMDMH, of propylene glycol in the range of about 0.09 to about 0.26 wt %, and of methyl paraben in the range of about 0.03 to about 0.09 wt %.

The data show that while all three use concentrations of paraben containing solution were microbiologically effective, the effectiveness of the paraben containing solution at a use concentration below about 0.6 wt % was less than that of the IPBC containing inventive solution (4A) at substantially the same usage level of DMDMH. These data demonstrate the superiority of the inventive antimicrobial solution (4A) containing DMDMH, phenoxyethanol and IPBC over an antimicrobial solution containing DMDMH, propylene glycol and paraben in an aqueous medium containing such known paraben inactivating ingredients as the Polysorbate 80 and proteinaceous material.

For further comparison, a third series of model mild shampoos were prepared employing a commercial aqueous solution of 55% DMDMH (MACKSTAT® DM, McIntyre Group, Ltd., University Park, Ill.) to separately contain, on a total shampoo basis, a concentration of DMDMH of about 0.12 wt %, about 0.24 wt % and about 0.36 wt %. The microbial efficacy of the DMDMH in the model shampoos was assessed during the foregoing modified microbial challenge test and the average antimicrobial efficacy data are shown in Table 9.

TABLE 9

| Model Shampoo w/% MACKSTAT® DM | Org. | Colony Forming Units (cfu/ml) | | | |
|---|---|---|---|---|---|
| | | Day 1 | Day 7 | Day 8 | Day 14 |
| 0.12 | An | 250,000 | 2,000 | 170,000 | 2,100 |
| | Ca | 180,000 | 10,000 | 49,000 | 34,000 |
| | Sa,Pa,Ec | 4,800 | 120 | 1,900 | 40 |
| 0.24 | An | 660 | <10 | 4,600 | 20 |
| | Ca | 580 | 20 | 1,900 | 250 |
| | Sa,Pa,Ec | 370 | <10 | 570 | <10 |
| 0.36 | An | 40 | <10 | 1,400 | <10 |
| | Ca | <10 | <10 | <10 | <10 |
| | Sa,Pa,Ec | <100 | <10 | 670 | <10 |
| 0 (control) | An | 710,000 | 690,000 | >3 × $10^6$ | 1.3 × $10^6$ |
| | Ca | 60,000 | 98,000 | 1,300 | 57,000 |
| | Sa,Pa,Ec | 13,000 | >3 × $10^6$ | >3 × $10^6$ | >3 × $10^6$ |

On a total shampoo basis, the three use concentrations of DMDMH respectively represented, on an active basis, a usage concentration of DMDMH in the range of about 0.06 to about 0.2 wt %. The data show that, while all three concentrations were microbiologically effective, the antifungal effectiveness of DMDMH at a usage level of 0.14% or less was not as effective as that of the IPBC containing inventive solution (4A) at substantially the same equivalent usage level of DMDMH.

EXAMPLE 5

This example illustrates the antimicrobial effectiveness of a liquid antimicrobial solution (5A) of this invention prepared generally by the in situ procedure of Example 1 to contain about 35 wt % DMDMH, about 56 wt % phenoxyethanol, about 0.5 wt % IPBC and about 8.5 wt % water when used in an aqueous model shampoo medium particularly prone to bacterial growth. The model shampoo contained known paraben inactivating ingredients and had the composition shown in Table 10. The efficacy of the inventive antimicrobial solution was compared to that of a commercial dry blend of DMDMH and IPBC.

TABLE 10

| Component | Weight Percent |
|---|---|
| Sodium laurylethersulfate | 5 |
| Disodium oleamido MEA sulfosuccinate | 2.8 |
| Disodium cocamphodiacetate | 3 |
| Cocamidopropyl betaine | 1 |
| Hydrolyzed collagen (Note c, Table 1) | 3.5 |
| Polysorbate 80 | 4 |
| Water | 80.7 |

A series of separate model shampoos were prepared containing, on a total shampoo basis, 0% (unpreserved control), about 0.2 wt %, about 0.4 wt %, about 0.6 wt % and about 0.8 wt % of the inventive liquid antimicrobial solution (5A), heating as needed to form a substantially clear product shampoo. The microbial efficacy was assessed by following the procedure of the modified microbial challenge test of Example 3. The average antimicrobial efficacy data for the inventive liquid antimicrobial solution (5A) after day 7 and, after rechallenge on day 14 was as shown in Table 11.

TABLE 11

| % Liq. (5A) in Model Shampoo | Org. | Colony Forming Units (cfu/ml) | |
|---|---|---|---|
| | | Day 7 | Day 14 |
| 0.2 | An | 230,000 | 378,000 |
| | Ca | 4,500 | 98,000 |
| | Sa,Pa,Ec | 1,600 | >3 × 10$^6$ |
| 0.4 | An | 14,000 | 68,000 |
| | Ca | <100 | <100 |
| | Sa,Pa,Ec | 200 | 980 |
| 0.6 | An | 20,000 | 2,100 |
| | Ca | <100 | <100 |
| | Sa,Pa,Ec | 250 | 20 |
| 0.8 | An | <100 | <100 |
| | Ca | <100 | <100 |
| | Sa,Pa,Ec | 10 | <10 |
| 0 (control) | An | 100,000 | 380,000 |
| | Ca | 39,000 | 160,000 |
| | Sa,Pa,Ec | >3 × 10$^6$ | >3 × 10$^6$ |

On a total shampoo basis, the four use concentrations of the inventive antimicrobial solution (5A) in the model shampoo respectively represented, on an active basis, a usage concentration of DMDMH in the range of about 0.07 to about 0.28 wt %, of phenoxyethanol in the range of about 0.112 to about 0.45 wt %, and of IPBC in the range of about 0.001 to about 0.004 wt %. A high antifungal effectiveness of the inventive antimicrobial solution (5A), especially against Ca, was noted at about 0.001 wt % IPBC usage level. Broad spectrum antibacterial activity was substantially achieved with the inventive solution (5A) at a use concentration of about 0.4 to about 0.8 wt %.

Included for comparison, a second series of model shampoos were prepared employing a commercial preservative powder blend, (GLYDANT PLUS®, Lonza, Inc., Fair Lawn, N.J., described generally in U.S. Pat. No. 4,844,891, reportedly containing 95% DMDMH and 5% IPBC). On a total shampoo basis, the model shampoos were prepared to contain the commercial dry powder blend at a use concentration of about 0.05 wt %, about 0.1 wt %, about 0.15 wt %, about 0.2 wt % and about 0.25 wt %. The average antimicrobial effectiveness of the powder blend was assessed during the same foregoing modified microbial challenge study and the average antimicrobial efficacy data was as shown in Table 12.

TABLE 12

| Test Shampoo wt % GLYDANT PLUS ® | Org. | Colony Forming Units (cfu/ml) | |
|---|---|---|---|
| | | Day 7 | Day 14 |
| 0.05 | An | 49,000 | 97,000 |
| | Ca | 100,000 | 1,400 |
| | Sa,Pa,Ec | >3 × 10$^6$ | >3 × 10$^6$ |
| 0.1 | An | 2,600 | 8,400 |
| | Ca | <100 | <100 |
| | Sa,Pa,Ec | 970 | 33,100 |
| 0.15 | An | 2,000 | 3,000 |
| | Ca | <100 | <100 |
| | Sa,Pa,Ec | 270 | 850 |
| 0.2 | An | <1,000 | 2,000 |
| | Ca | <10 | <10 |
| | Sa,Pa,Ec | 90 | 50 |
| 0.25 | An | <1,000 | <10 |
| | Ca | <1,000 | <10 |
| | Sa,Pa,Ec | 10 | 20 |
| 0 (control) | An | 100,000 | 380,000 |
| | Ca | 39,000 | 160,000 |
| | Sa,Pa,Ec | >3 × 10$^6$ | >3 × 10$^6$ |

On a total shampoo basis, the five concentrations of the commercial powder blend respectively represented, on an active basis, a usage concentration of DMDMH in the range of about 0.048 to about 0.23 wt %, and a usage concentration of IPBC in s range of about 0.0025 to about 0.0125 wt %.

The data show that the inventive antimicrobial solution (5A) was superior to the commercial powder blend at equivalent DMDMH or equivalent IPBC concentration by achieving antifungal and broad spectrum antimicrobial activity at a lower MEL concentration.

The foregoing examples demonstrate that the liquid antimicrobial solutions of this invention surprisingly were more effective in achieving substantially broad spectrum microbial reduction than liquid antimicrobial solutions of paraben containing DMDMH prepared in a phenoxyethanol or propylene glycol medium at a lower usage concentration of antifungal component. For example, the efficacy achieved in controlling Ca within 7 days at a concentration of about 0.4 wt % with inventive antimicrobial solution was substantially equivalent to that of a concentration of about 0.5 wt % of commercial paraben containing antimicrobial solutions of the '722 patent and the '843 patent and of about 0.05 wt % of the commercial powder blend of DMDMH and IPBC at an equivalent IPBC concentration.

Thus, the enhanced antimicrobial efficacy of the inventive solutions observed in this comparative study was surprising.

The present invention has been described generally and with respect to preferred embodiments. It will be understood that modifications and variation of the disclosed method and compositions may be made without departing from the spirit and scope of the novel concept of the present invention.

What is claimed is:

1. A liquid antimicrobial solution for use as a preservative composition made by combining on a total solution weight basis components comprising:

(A) a 5,5-disubstituted hydantoin which has in at least one of the 1 and 3 positions a methylol substituent, said methylol substituent being present in both said 1 and 3 positions in at least about 10 weight percent of the total weight of said methylol substituted 5,5-disubstituted hydantoin and wherein each of said 5,5 substituents is selected from the group consisting of phenyl and lower alkyl groups;

(B) a liquid aromatic alcohol having the formula:

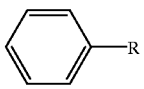

where R is selected from the group consisting of:

—CH$_2$OH,   —OCH$_2$OH,   —OCH$_2$CH$_2$OH,

—CH$_2$CH$_2$OH,   —OC$_3$H$_6$OH, and   —C$_3$H$_6$OH;

(C) an iodoalkynyl alkyl carbamate having the formula:

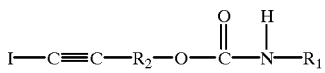

where: R$_1$ is an alkyl group containing no more than 20 carbon atoms, and R$_2$ is an alkylene group containing from 1 through 4 carbon atoms; and (D) less than about 15 weight percent water.

2. The antimicrobial solution of claim 1 wherein said combination is made by preparing methylol substituted 5,5-disubstituted hydantoin in situ in a liquid medium comprising said aromatic alcohol by thermally reacting dissolved formaldehyde with dissolved 5,5-disubstituted hydantoin, and then dissolving said iodoalkynyl alkyl carbamate in a solution comprising said so in situ prepared methylol substituted 5,5-disubstituted hydantoin dissolved in said aromatic alcohol.

3. The antimicrobial solution of claim 1 wherein the weight ratio of component (A) to component (C) is in the range of from about 60:1 to about 80:1.

4. The antimicrobial solution of claim 1 wherein component (A) comprises at least 25 weight percent 1,3-dimethylol-5,5-dimethyl hydantoin on a 100 weight percent total methylol substituted 5,5-disubstituted hydantoin basis.

5. The antimicrobial solution of claim 1 wherein said aromatic alcohol is selected from the group consisting of phenoxyethanol, benzyl alcohol, phenethyl alcohol, phenoxyisopropyl alcohol and mixtures thereof.

6. The antimicrobial solution of claim 1 wherein component (B) comprises phenoxyethanol.

7. The antimicrobial solution of claim 1 wherein said iodoalkynyl alkyl carbamate is 3-iodo-2-propynyl butyl carbamate.

8. The antimicrobial solution of claim 1 wherein on a 100 percent solution basis, component (A) comprises at least 30 weight percent 1,3-dimethylol-5,5-dimethyl hydantoin, component (B) comprises at least 50 weight percent phenoxyethanol, component (C) comprises 3-iodo-2-propynyl butyl carbamate and the weight ratio of component (A) to component (C) is in the range of from about 65:1 to about 78:1.

9. The antimicrobial solution of claim 8 wherein the weight ratio of component (A) to component (C) is in the range of from about 70:1 to about 75:1.

10. A liquid antimicrobial solution for use as a preservative composition comprising, on a 100 weight percent basis:

(A) from about 20 to about 75 weight percent of a 5,5-disubstituted hydantoin which has in at least one of the 1 and 3 positions a methylol substituent, said methylol substituent being present in both said 1 and 3 positions in at least about 10 weight percent of the total weight of said methylol substituted 5,5-disubstituted hydantoin and wherein each of said 5,5 substituents is selected from the group consisting of phenyl and lower alkyl groups;

(B) from about 20 to about 70 weight percent of a liquid aromatic alcohol having the formula:

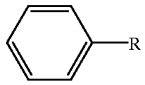

where R is selected from the group consisting of:

—CH$_2$OH,   —OCH$_2$OH,   —OCH$_2$CH$_2$OH,

—CH$_2$CH$_2$OH,   —OC$_3$H$_6$OH, and   —C$_3$H$_6$OH;

(C) an antifungally effective amount of iodoalkynyl alkyl carbamate having the formula:

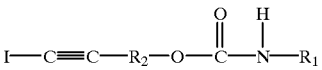

where: R$_1$ is an alkyl group containing no more than 20 carbon atoms, and R$_2$ is an alkylene group containing from 1 through 4 carbon atoms;

(D) less than 15 weight percent water and the weight ratio of said methylol substituted 5,5-disubstituted hydantoin to said carbamate is in the range of from about 60:1 to about 80:1.

11. The antimicrobial solution of claim 10 wherein said methylol substituted 5,5-disubstituted hydantoin has been prepared in situ in said aromatic alcohol by thermally reacting dissolved formaldehyde with dissolved 5,5-disubstituted hydantoin, and said iodoalkynyl alkyl carbamate having been separately prepared is then dissolved in a solution comprising said so in situ prepared methylol substituted 5,5-disubstituted hydantoin dissolved in said aromatic alcohol.

12. The antimicrobial solution of claim 10 wherein said methylol substituted 5,5-disubstituted hydantoin comprises 1,3-dimethylol-5,5-dimethyl hydantoin.

13. The antimicrobial solution of claim 10 wherein said aromatic alcohol is selected from the group consisting of phenoxyethanol, benzyl alcohol, phenethyl alcohol, phenoxyisopropyl alcohol and mixtures thereof.

14. The antimicrobial solution of claim 10 wherein the iododalkynyl alkyl carbamate comprises about 0.25 to about 1.25 weight percent of 3-iodo-2-propynyl butyl carbamate.

15. The antimicrobial solution of claim 10 wherein the 5,5-disubstituted hydantoin comprises at least 30 weight percent 1,3-dimethylol-5,5-dimethyl hydantoin, said aromatic alcohol comprises at least 50 weight percent phenoxyethanol and said iodoalkynyl alkyl carbamate comprises 3-iodo-2-propynyl butyl carbamate.

16. A process for preparing a liquid antimicrobial solution comprising a liquid aromatic alcohol that contains (i) a methylol substituted 5,5-disubstituted hydantoin which comprises at least 10 weight percent, on a 100 weight percent total methylol substituted 5,5-disubstituted hydantoin basis, 1,3-dimethylol-5,5-disubstituted hydantoin and wherein each of said 5,5 substituents is selected from the group consisting of phenyl and lower alkyl groups, and (ii) an iodoalkynyl alkyl carbamate having the formula:

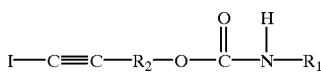

where: $R_1$ is an alkyl group containing no more than 20 carbon atoms, and $R_2$ is an alkylene group containing from 1 through 4 carbon atoms, said process comprising the steps of:
(a) dissolving a formaldehyde selected from the group consisting of paraformaldehyde and formalin in at least one liquid aromatic alcohol having the formula:

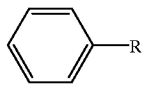

where R is selected from the group consisting of:

—$CH_2OH$, —$OCH_2OH$, —$OCH_2CH_2OH$,

—$CH_2CH_2OH$, —$OC_3H_6OH$, and —$C_3H_6OH$ to provide a liquid medium;
(b) heating said liquid medium to a temperature of no more than about 50° C. to provide a heated liquid medium;
(c) admixing into said heated liquid medium said 5,5-disubstituted hydantoin to provide a reaction mixture, the amount of said 5,5-disubstituted hydantoin so admixed being sufficient to produce in said reaction mixture an initial calculated mole ratio of formaldehyde to said 5,5-disubstituted hydantoin of from about 1:1 to about 3:1;
(d) further heating under autogenous conditions said reaction mixture to a temperature of no more than 110° C. and maintaining said temperature until said 1,3-dimethylol 5,5-disubstituted hydantoin is produced;
(e) cooling said resulting reaction mixture to a temperature range between from about 25° C. to no more than about 40° C.; and
(f) dissolving in said so-cooled resulting reaction mixture said iodoalkynyl alkyl carbamate in an amount being sufficient to produce on a resulting total antimicrobial solution basis a weight ratio of said 1,3-dimethylol 5,5-disubstituted hydantoin to said iodoalkynyl alkyl carbamate in the range of from about 60:1 to about 80:1.

17. The process of claim 16 wherein said antimicrobial solution additionally contains water in a total amount of no more than about 15 weight percent, total solution weight basis, a portion of said water having been added in at least one of steps (a) through (f).

18. The process of claim 16 wherein said methylol substituted 5,5-disubstituted hydantoin comprises 1,3-dimethylol-5,5-dimethyl hydantoin.

19. The process of claim 16 wherein said aromatic alcohol is selected from the group consisting of phenoxyethanol, benzyl alcohol, phenethyl alcohol, phenoxyisopropyl alcohol and mixtures thereof.

20. The process of claim 16 wherein said iodoalkynyl alkyl carbamate comprises 3-iodo-2-propynyl butyl carbamate.

21. The resulting antimicrobial solution produced by the process of claim 16.

22. The resulting antimicrobial solution produced by the process of claim 17 wherein on a 100 weight percent solution basis:
(a) said methylol substituted 5,5-disubstituted hydantoin comprises from about 20 to about 75 weight percent 1,3-dimethylol-5,5,-dimethyl hydantoin;
(b) said aromatic alcohol comprises from about 20 to about 70 weight percent phenoxyethanol;
(c) the amount of water is no more than about 10 weight percent; and the weight ratio of said methylol substituted 5,5-disubstituted hydantoin to said carbamate is in the range of from about 65:1 to about 78:1.

23. A method of inhibiting or retarding microbial growth in a medium capable of supporting microorganism growth comprising incorporating into said medium an antimicrobially effective amount of said antimicrobial solution of claim 1.

24. A method of inhibiting or retarding microbial growth in a medium capable of supporting microorganism growth comprising incorporating into said medium an antimicrobially effective amount of said antimicrobial solution of claim 10.

25. A method of inhibiting or retarding microbial growth in a medium capable of supporting microorganism growth comprising incorporating into said medium an antimicrobially effective amount of said resulting antimicrobial solution of claim 21.

26. A method of inhibiting or retarding microbial growth in a medium capable of supporting microorganism growth comprising incorporating into said medium an antimicrobially effective amount of said resulting antimicrobial solution of claim 22.

* * * * *

UNITED STATES PATENT AND TRADEMARK OFFICE
CERTIFICATE OF CORRECTION

PATENT NO : 5,965,594
DATED : October 12, 1999
INVENTOR(S): Thomas G. Schoenberg et al.

It is certified that error appears in the above-identified patent and that said Letters Patent is hereby corrected as shown below:

Column 11, line 29, delete "105 to 106" and insert --$10^5$ to $10^6$--.

Signed and Sealed this

Second Day of May, 2000

Q. TODD DICKINSON

*Attest:*

*Attesting Officer*   *Director of Patents and Trademarks*